(12) United States Patent
Pearson et al.

(10) Patent No.: US 6,284,919 B1
(45) Date of Patent: Sep. 4, 2001

(54) PROCESS FOR CARBONYLATION OF ETHYLENE

(75) Inventors: Jean Margaret Pearson, Cleveland; Raymond Anthony Hadden, Durham, both of (GB)

(73) Assignee: Imperial Chemical Industries PLC, London (GB)

(*) Notice: Subject to any disclaimer, the term of this patent is extended or adjusted under 35 U.S.C. 154(b) by 0 days.

(21) Appl. No.: 09/396,637

(22) Filed: Sep. 15, 1999

Related U.S. Application Data

(63) Continuation of application No. PCT/GB98/00629, filed on Feb. 27, 1998.

(30) Foreign Application Priority Data

Mar. 19, 1997 (GB) .................................................. 9705699

(51) Int. Cl.[7] .............................. C07C 67/38; C07C 51/14
(52) U.S. Cl. ........................................... 560/233; 562/522
(58) Field of Search .............................. 560/233; 562/522

(56) References Cited

U.S. PATENT DOCUMENTS

| | | | |
|---|---|---|---|
| 4,269,781 | * | 5/1981 | Vanderspurt et al. . |
| 4,960,926 | * | 10/1990 | Drent . |
| 5,364,957 | * | 11/1994 | Arnoldy et al. . |

FOREIGN PATENT DOCUMENTS

| | | |
|---|---|---|
| 0 411 721 | 2/1991 | (EP) . |
| 96 19434 | 6/1996 | (WO) . |

OTHER PUBLICATIONS

Keim et al. (J. Organomet. Chem.; 1996; 514(1–2), pp. 271–276).*

* cited by examiner

*Primary Examiner*—Paul J. Killos
*Assistant Examiner*—Robert W. Deemie
(74) *Attorney, Agent, or Firm*—Pillsbury Winthrop LLP

(57) ABSTRACT

A process for the liquid-phase carbonylation of ethylene, according to the equation $C_2H_4+CO+ROH \rightarrow C_2H_5CO_2R$, in the presence of a catalyst system comprising a Group VIII metal or compound thereof, a phosphine ligand and a source of anions, and in the presence of water or a source of organic hydroxyl groups, is carried out in conditions in which the molar ratio of ethylene to carbon monoxide in the gaseous phase of the reactor is greater than 1:1. The higher ratios of ethylene to carbon monoxide are beneficial in increasing the turnover number of the catalyst system.

19 Claims, No Drawings

PROCESS FOR CARBONYLATION OF ETHYLENE

This is a continuation under 35 U.S.C. Section 120 of International application Ser. No. PCT/GB98/00629 filed on Feb. 27. 1998 which application designates the US.

FIELD OF THE INVENTION

The invention relates to the carbonylation of ethylene using carbon monoxide.

BACKGROUND OF THE INVENTION

The carbonylation of ethylene using carbon monoxide in the presence of an alcohol or water and a catalyst system comprising a Group VIII metal, e.g. palladium, and a phosphine ligand, e.g. an alkyl phosphine, cycloalkyl phosphine, aryl phosphine, pyridyl phosphine or bidentate phosphine, has been described in numerous European patents and patent applications, e.g. EP-A-0055875, EP-A-04489472, EP-A-0106379, EP-A-0235864, EP-A0274795, EP-A-0499329, EP-A-0386833, EP-A-0441447, EP-A-0489472, EP-A-0282142, EP-A-0227160, EP-A-0495547 and EP-A-0495548. In particular, EP-A0227160, EP-A-0495547 and EP-A-0495548 disclose that bidentate phosphine ligands provide catalyst systems which enable higher reaction rates to be achieved.

A problem with the previously disclosed catalyst systems is that although relatively high reaction rates can be achieved, the catalyst dies off quickly which necessitates the frequent replenishment of the catalyst and hence results in a process which is industrially unattractive.

WO 96/19434 disdoses a particular group of bidentate phosphine compounds which can provide remarkably stable catalysts which require little or no replenishment and the use of such bidentate catalysts in a process for the carbonylation of ethylene with carbon monoxide.

DETAILED DESCRIPTION OF THE INVENTION

It has now been found that, when used in the process for the carbonylation of ethylene with carbon monoxide, the activity and life of catalyst systems based on such phosphine compounds are very sensitive to the relative amounts of ethylene and carbon monoxide in the gaseous phase of the reactor. This is counter to the common teaching in the art which generally does not express any preference for the relative amounts of these reactants.

Surprisingly therefore, it has now been found that the activity and the life of the catalyst, when used in a liquid phase carbonation process, can be significantly improved by using a high molar ratio of ethylene to carbon monoxide in the gas in contact with the liquid phase.

Accordingly, the present invention provides a process for the carbonylation of ethylene in a liquid phase, which process comprises (i) forming a gaseous phase from an ethylene feed stream and a carbon monoxide feed stream;

(ii) contacting the gaseous phase with a catalyst system within the liquid phase containing a source of hydroxyl groups. said catalyst system comprising palladium, or a compound thereof, and a phosphine ligand together with a source of anions; and (iii) reacting the ethylene with the carbon monoxide in the presence of the source of hydroxyl groups and of the catalyst system characterised in that the ethylene feed stream and carbon monoxide feed stream provide a molar ratio of ethylene to carbon monoxide in the gaseous phase which is greater than 1:1.

The carbon monoxide may be used in the presence of other gases which are inert in the reaction. Examples of such gases include hydrogen, nitrogen, carbon dioxide and the noble gases such as argon.

The molar ratio of the ethylene to carbon monoxide in the gaseous phase, hereinafter termed the gaseous phase molar ratio, is greater than 1:1, preferably at least 3:1, particularly at least 5:1, especially from 5:1 to 50:1 and particularly especially from 7:1 to 15:1. Operating the process of the present invention with a gaseous phase molar ratio of less than 5:1, particularly of less than 3:1 and especially of less than 1:1 leads to a rapid deterioration in the performance of the catalyst.

It is believed that an important factor that influences the life of the catalyst system is the molar ratio of ethylene to carbon monoxide dissolved in the liquid phase, herein after termed the liquid phase molar ratio. The liquid phase molar ratio may differ from the gaseous phase molar ratio due to the different solubilities of ethylene and carbon monoxide in the liquid phase. The solubilities of ethylene and carbon monoxide in the liquid phase are dependent on factors such as the temperature, pressure and composition of the liquid phase. Consequently, in order to achieve the required liquid phase molar ratio, the gaseous phase molar ratio may need to be adjusted to compensate for such factors. Preferably, the gaseous phase molar ratio should be adjusted such that a liquid phase molar ratio of at least 5:1 is maintained.

The ratio of the number of moles of ethylene to the number of moles of carbon monoxide fed to the reactor by the ethylene feed stream and carbon monoxide feed stream in order to maintain the desired molar ratio of ethylene to carbon monoxide in the gaseous phase will depend on the reactor design. Where the gaseous phase is recycled after contact with the liquid phase then the ethylene and carbon monoxide feed streams are used to replenish the ethylene and carbon monoxide consumed during the carbonylation reaction and the ethylene and carbon monoxide that is removed with any offtake from the liquid phase. Thus, the ratio of the number of moles of ethylene to the number of moles of carbon monoxide fed by the feed streams is approximately 1:1. Alternatively, where the gaseous phase is not fully recycled then the ratio of the number of moles of ethylene to the number of moles of carbon monoxide fed by the feed streams will more closely match the desired molar ratio in the gaseous phase.

The feeds of ethylene and carbon monoxide may be continuous, intermittent or batch. Preferably, the initial feed into the reactor is of ethylene. This further reduces the poisoning of the catalyst system by the carbon monoxide.

The process of the present invention is preferably carried out at a temperature from 20 to 250° C., in particular from 40 to 150° C. and especially from 70 to 120° C.

The process may be conducted under a total pressure of from $1 \times 10^5$ to $100 \times 10^5$ $N.m^{-2}$ and in particular from $5 \times 10^5$ to $50 \times 10^5$ $N.m^{-2}$.

A preferred phosphine ligand is a bidentate phosphine of general formula (I)

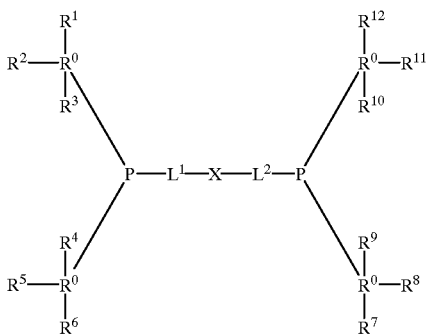

(I)

wherein $R^0$ is a tertiary carbon atom each of $R^1, R^2, R^3, R^4, R^5, R^6, R^7, R^8, R^9, R^{10}, R^{11}$, and $R^{12}$ is independently a pendant optionally substituted organic group which carries a carbon atom through which the group is linked to the respective $R^0$;

each of $L^1$ and $L^2$ is independently a linking group selected from an optionally substituted lower alkylene chain connecting the respective phosphorus atom to the group, X; and X is a bridging group comprising an optionally substituted aryl moiety to which the phosphorus atoms are linked on available adjacent carbon atoms.

The pendant optionally substituted organic groups of the preferred catalyst system, $R^1, R^2, R^3, R^4, R^5, R^6, R^7, R^8, R^9, R^{10}, R^{11}$ and $R^{12}$, may be independently selected from a wide range of components. Preferably, the pendant groups are optionally substituted lower alkyl, e.g. $C_{1-8}$, and may be branched or linear.

Particularly preferred is when the organic groups, $R^1, R^2, R^3, R^4, R^5, R^6, R^7, R^8, R^9, R^{10}, R^{11}$ and $R^{12}$, when associated with their respective $R^0$ carbon atom, form composite groups which are at least as sterically hindering as t-butyl. Steric hindrance in this context is as discussed at page 14 et seq of "Homogeneous Transition Metal Catalysis—A Gentle Art", by C Masters, published by Chapmnan and Hall, 1981.

The linking groups, $L^1$ and $L^2$, are independently selected from an optionally substituted, particularly lower alkyl or lower alkylene, e.g. $C_1$ to $C_4$, chain. Especially preferred is when both $L^1$ and $L^2$ are methylene.

The bridging group X is an aryl moiety, e.g. a phenyl group, which may be optionally substituted, provided that the two phosphorus atoms are linked to adjacent carbon atoms, e.g. at the 1 and 2 positions on the phenyl group. Optional substitution of the aryl moiety may be by other organic groups, e.g. alkyl, particularly $C_{1-8}$, aryl, alkoxy, carbalkoxy, halo, nitro, trihalomethyl and cyano. Furthermore, the aryl moiety may be a fused polycyclic group, e.g. naphthalene, biphenylene or indene.

Examples of suitable bidentate ligands are α,α'-bis(di-t-butyl phosphino)-o-xyleite (also known as 1,2-bis(di-t-butylphosphinomethyl)benzene), α,α'-bis(dineopentyl phosphino)-o-xlene and 2,3-bis(di-t-butylphosphinomethyl) naphthalene. Additionally, the bidentate phosphine may be bonded to a suitable polymeric or inorganic substrate via at least one of the bridging group X, the linking group $L^1$ or the linking group $L^2$, e.g. α,α'-bis(di-t-butyl phosphino)-o-xylene may be bonded via the xylene group to polystyrene to give an immobile heterogeneous catalyst.

Preferably, the bidentate ligand is present in an amount such that the ratio of the number of moles of the bidentate ligand present to the number of moles of palladium present is from 1 to 50, e.g. 1 to 10 and particularly from 1 to 5 mol per mol.

Suitable compounds of palladium include salts of palladium with, or compounds comprising weakly co-ordinated anions derived from, nitric acid; sulphuric acid; lower alkanoic (up to $C_{12}$) acids such as acetic acid and propionic acid including halogenated carboxylic acids such as trifluoroacetic acid and trichloroacetic acid; sulfonic acids such as methanesulfonic acid, chlorosulfonic acid, fluorosulfonic acid, trifluoromethanesulfonic acid, benzenesulfonic acid, naphthalene sulfonic acid, toluenesulfonic acids, e.g. p-toluenesulfonic acid, t-butylsulfonic acid, and 2-hydroxypropanesulfonic acid; sulfonated ion exchange resins; perhalic acids such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenyl borate derivatives, e.g. perfluorotetraphenyl borate. Additionally, zerovalent palladium complexes particularly those with labile ligands, e.g. triphenylphosphine or alkenes such as dibenzylideneacetone or styrene may be used.

The anion may be introduced as one or more of an acid having a pKa measured in aqueous solution of less than 4, a salt with a cation that does not interfere with the reaction, e.g. metal salts or largely organic salts such as alkyl ammonium, and a precursor, such as an ester, that can break down under reaction conditions to generate the anion in situ. Suitable acids and salts include the acids and salts, other than unsubstituted carboxylates, listed supra.

The quantity of anion present is not critical to the catalytic behaviour of the catalyst system. The molar ratio of anion to palladium may be from 1:1 to 500:1, preferably from 2:1 to 100:1 and particularly from 3:1 to 30:1. Where the anion is provided by a combination of acid and salt, the relative proportion of the acid and salt is not critical.

The catalyst system may be used homogeneously or heterogeneously. Preferably the catalyst system is used homogeneously.

The catalyst system is preferably constituted in the liquid phase which may be formed by one or more of the reactants or by the use of a suitable solvent.

Suitable solvents that may be used in conjunction with the catalyst system include one or more aprotic solvents such as ethers, e.g. diethyl ether, dimethyl ether of diethylene glycol, anisole and diphenyl ether, aromatic compounds, including halo variants of such compounds, e.g. benzene, toluene, ethyl benzene, o-xylene, m-xylene, p-xylene, chlorobenzene, o-dichlorobenzene, m-dichlorbenzene, and p-dichlorobenzene; alkanes, including halo variants of such compounds, e.g. hexane, heptane, 2, 2, 3-trimethylpentane, methylene chloride and carbon tetrachloride; nitrites, e.g. benzonitrile and acetortile; esters, e.g. methyl benzoate, methyl acetate, methyl propionate and dimethyl phthalate; sulfones, e.g. diethyl sulfone and tetrahydrothiophene 1, 1-dioxide; carboxylic acids, e.g. propionic acid. It is preferred to use as a solvent a compound which takes part in the reaction either as a reactant or a product, to minimise the number of different compounds present in the liquid phase to facilitate separation of the mixture. Therefore in the example when ethylene and carbon monoxide are carbonylated in the presence of methanol to form methyl propionate, a particularly suitable solvent is methyl propionate.

The end product of the reaction is determined at least in part by the source of hydroxyl groups that is used. The use of water gives rise to the corresponding carboxylic acid whereas the use of an alkanol leads to the corresponding ester. Suitable alkanols include $C_{1-30}$ alkanols, optionally substituted with one or more substituents such as halogen atoms, cyano, carbonyl, alkoxy or aryl groups. Suitable alkanols include one or more of methanol, ethanol, propanol, 2-propanol, 2-butanol, t-butyl alcohol and chiorocapryl alcohol. Particularly useful are methanol and ethanol. Addionally or alternatively, poldroxyl compounds, such as diols and sugars, may be used.

The molar ratio of the amount of ethylene used in the reaction to the amount of hydroxyl providing compound is not critical and may vary between wide limits, e.g. from 0.001:1 to 100:1 mol/mol in the liquid phase.

The process of the invention is particularly suitable for the production of methyl propionate. In one preferred embodiment therefore we provide a process for the production of methyl propionate comprising the steps of:

(i) forming a gaseous phase from an ethylene feed stream and a carbon monoxide feed stream;

(ii) contacting the gaseous phase with a catalyst system within a liquid phase comprising methanol, a solvent and a catalyst system comprising palladium, or a compound thereof, a phosphine ligand and a source of anions; and (iii) reacting the ethylene with the carbon monoxide in the presence of the methanol and of the catalyst system; characterised in that the ethylene feed stream and carbon monoxide feed stream provide a molar ratio of ethylene to carbon monoxide in the gaseous phase which is greater than 1:1.

Preferred catalyst systems are those described above. Preferably the solvent comprises methanol, methyl propionate or a mixture thereof.

The following Examples further illustrate the present invention.

EXAMPLES

Example 1

A reactant solution for a series of experiments was made up of Pd(L-L)dba (92 mg, $1.25 \times 10^{-4}$ moles), where L-L is 1,2-bis(di-t-butylphosphinomethyl)benzene and dba is dibenzyrlideneacetone dissolved in methanol (100 mls, 2.47 moles) and methyl propionate (200 mls, 2.08 moles). Methanesulfonic acid was also added in various amounts as shown in the table below.

The reaction was conducted in a two-litre Hastelloy B2 autoclave. The autoclave was evacuated and then charged with the reactant solution, before being heated to 80° C.

When at temperature, ethylene was added to the autoclave to the pressure given in the Table 1 whereupon carbon monoxide was added to make a total pressure of $10^6$ N.m$^{-2}$. A reservoir of reactant gases containing a 1:1 molar ratio of ethylene to carbon monoxide fed the autoclave via a regulator to maintain the operating pressure within the autoclave constant at a total pressure of $10^6$ N.m-2 (gauge), and to maintain the gaseous molar ratio in the head space above the liquid phase at that set by the initial admission of ethylene and carbon monoxide. The system was therefore operated in a semi-batch manner.

TABLE 1

| MeSO$_3$H (ml) | Ethylene (bar) | Carbon monoxide (bar) | Ethylene: Carbon Monoxide | Moles of Methyl Propionate after 180 Minutes |
|---|---|---|---|---|
| 0.03 | 2.5 | 7.5 | 1:3 | 0.42 |
| 0.03 | 7.5 | 2.5 | 3:1 | 0.56 |
| 0.1 | 2.5 | 7.5 | 1:3 | 0.5 |
| 0.1 | 7.5 | 2.5 | 3:1 | 0.77 |

Example 2

A reactant solution was made up of Pd(L-L)dba (20 mg, $2.7 \times 10^{-5}$ moles) dissolved in methanol (73 mls, 1.8 moles) and methyl propionate (27 mls, 0.28 moles) with a ten-fold molar excess (to palladium) of methanesulfonic acid (1.75x10-2 mis, $2.7 \times 10^{-4}$ moles).

The experiments were conducted in a 300 ml stainless steel autoclave in a similar manner to that described in Example 1. The pressures of carbon monoxide and ethylene at which the reactor was charged before feeding the 1:1 molar mixture from the reservoir together with the amount of methyl propionate produced after 200 minutes is shown in Table 2.

It can be seen that increasing the ratio of the partial pressure of ethylene to the partial pressure of carbon monoxide generally increases the amount of methyl propionate produced at a given partial pressure of carbon monoxide.

TABLE 2

| Ethylene (bar) | Carbon monoxide (bar) | Ratio of Ethylene to Carbon Monoxide | Moles of Methyl Propionate after 200 Minutes |
|---|---|---|---|
| 10.1 | 0.5 | 20:1 | 0.42 |
| 9.5 | 0.6 | 16:1 | 0.45 |
| 9.7 | 3.3 | 3:1 | 0.34 |
| 9.5 | 6.3 | 1.5:1 | 0.23 |

Example 3

A reactant solution was made up of Pd(L-L)dba (37 mg, $5 \times 10^{-5}$ moles) dissolved in methanol (219 ml, 5.41 moles) and methyl propionate (81 ml, 0.841 moles) with methanesulfonic acid (0.068m1, 1.05 xl moies) added.

The experiments were conducted in a two-litre stainless steel autoclave in a similar manner to that described in Example 1. The pressures of carbon monoxide and ethylene at which the reactor was charged before feeding the 1:1 molar mixture from the reservoir together with the mole fraction of the gases in the liquid and the amount of methyl propionate produced after 240 minutes is shown in Table 3.

TABLE 3

| Ethylene (barg) | CO (barg) | Mole Fraction ethylene in liquid | Mole Fraction CO in liquid | Moles of Methyl Propionate after 240 minutes |
|---|---|---|---|---|
| 9 | 1 | $3.98 \times 10^{-2}$ | $7.1 \times 10^{-4}$ | 1.32 |
| 7 | 3 | $3.12 \times 10^{-2}$ | $2.14 \times 10^{-4}$ | 1.23 |
| 5 | 5 | $2.24 \times 10^{-2}$ | $3.59 \times 10^{-4}$ | 0.97 |
| 3 | 7 | $1.36 \times 10^{-2}$ | $5.06 \times 10^{-4}$ | 0.48 |
| 1 | 9 | $4.57 \times 10^{-3}$ | $6.56 \times 10^{-4}$ | 0.23 |

Example 4

The reaction was carried out in an agitated one-litre autoclave which was operated in a continuous manner. That is, the reactor was fed by separate supplies of carbon monoxide, ethylene and methanol and a dilute solution of the catalyst was also continuously added to the autoclave. The flow rate of the gases was controlled using mass flow controllers while both the methanol and catalyst solutions were fed to the solution by a calibrated Gilson pump. The level of liquid within the reactor was controlled at a constant level by a DP cell and any excess liquid (and the corresponding quantity of dissolved gas) was taken from the autoclave and flashed into a column. This column was also controlled to give a constant level within its reboiler. Hence, any excess liquid was purged from the top of the column while a solution containing the high boiling catalyst was recirculated to the reactor. The pressure within the reactor was maintained at a constant level by venting any excess gas, which was not consumed in the reaction or removed in the liquid flow to the column, from the head space of the autoclave. The composition of the reactor head space gas was monitored by on-line GC analysis.

The catalyst used, Pd[L-L].dba (as in Example 1), was continuously fed to the reactor as a dilute solution in methanol without exposure to air. The acid co-catalyst was methanesulfonic acid. A list of the other principal reaction parameters which were used is presented in Table 4.

The inlet ethylene and CO gas flows were varied during the experiment to vary the reactor headspace ratio. Table 5 gives the turnover number (i.e. the moles of methyl propionate produced per mole of catalyst fed at steady state) calculated at each headspace ethylene:CO ratio used.

TABLE 4

| Autoclave Temperature | 100° C. |
|---|---|
| Autoclave Pressure | 10 barg |
| Agitator Speed | 1000 rpm |
| Recirculation Rate | 5 L/hr |
| Methanol Feed Rate | 0.15 L/hr |
| Catalyst Feed Rate | 3 × 10$^{-6}$ moles/hr |
| Molar ratio of acid:palladium in feed solution | 20 |
| Total Gas Flow into Reactor | 200 L/hr |

TABLE 5

| Reactor headspace ethylene/CO ratio | Turnover number (molesMeP/molePd) |
|---|---|
| 0.72 | 40000 |
| 1.08 | 53333 |
| 1.8 | 60000 |
| 3.6 | 80000 |
| 7 | 88667 |

What is claimed is:

1. A process for the carbonylation of ethylene in a liquid phase which process comprises
   (i) forming a gaseous phase from an ethylene feed stream and a carbon monoxide feed stream;
   (ii) contacting the gaseous phase with a catalyst system within the liquid phase containing water or a source of organic hydroxyl groups, said catalyst system comprising palladium, or a compound thereof, and a phosphine ligand together with a source of anions; and
   (iii) reacting the ethylene with the carbon monoxide in the presence of the source of hydroxyl groups and of the catalyst system;
      wherein the ethylene feed stream and carbon monoxide feed stream provide a molar ratio of ethylene to carbon monoxide in the gaseous phase of the reactor which is greater than 1:1 and the source of anions is derivable from an acid with a pKa measured in aqueous solution of less than 4.

2. A process as claimed in claim 1 wherein the molar ratio of the ethylene to carbon monoxide in the gaseous phase is at least 3:1.

3. A process as claimed in claim 2 wherein the molar ratio of the ethylene to carbon monoxide in the gaseous phase is at least 5:1.

4. A process as claimed in claim 1 wherein the molar ratio of the ethylene to carbon monoxide in the liquid phase is at least 3:1.

5. A process as claimed in claim 4 wherein the molar ratio of the ethylene to carbon monoxide in the liquid phase is at least 5:1.

6. A process as claimed in claim 1 wherein the reaction is carried out at a temperature from 20 to 250° C.

7. A process for the carbonylation of ethylene in a liquid phase comprising:
   (iii) forming a gaseous phase from an ethylene feed stream and a carbon monoxide feed stream;
   (iv) contacting the gaseous phase with a catalyst system within the liquid phase containing water or a source of organic hydroxyl groups; and
   (iii) reacting the ethylene with the carbon monoxide in the presence of the source of hydroxyl groups and of the catalyst system;
      wherein the ethylene feed stream and carbon monoxide feed stream provide a molar ratio of ethylene to carbon monoxide in the gaseous phase of the reactor which is greater than 1:1 and said catalyst system comprises a combination of:
      (a) palladium or a compound thereof;
      (b) a bidentate phosphine represented by the general formula (1)

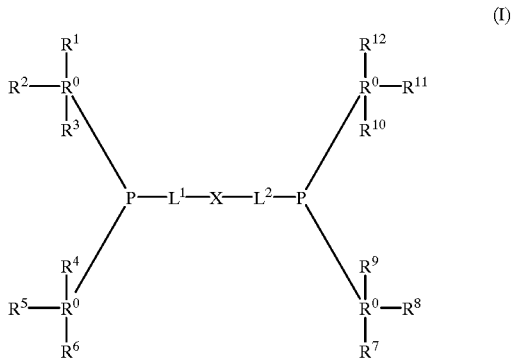

wherein
   $R^0$ represents a tertiary carbon atom,
   each of $R^1$, $R^2$, $R^3$, $R^4$, $R^5$, $R^6$, $R^7$, $R^8$, $R^9$, $R^{10}$, $R^{11}$ and $R^{12}$ independently represents a pendant optionally substituted $C_{1-8}$ hydrocarbon group which carries a carbon atom through which the group is linked to the respective $R^0$,
   each of $L^1$ and $L^2$ independently represents a linking group selected from an optionally substituted $C_{1-4}$ alkylene chain connecting the respective phosphorus atom to the group X, and
   X represents a bridging group comprising an optionally substituted aryl moiety to which the phosphorus atoms are linked on available adjacent carbon atoms; and (c) an anion which is essentially non-coordinating to palladium ions and derivable from an acid with a pKa measured in aqueous solution of less than 4.

8. A process as claimed in claim 7 wherein the pendant optionally substituted $C_{1-8}$ hydrocarbon groups, $R^1$, $R^2$, $R^3$, $R^4$, $R^5$, $R^6$, $R^7$, $R^8$, $R^9$, $R^{10}$, $R^{11}$ and $R^{12}$ are optionally substituted $C_{1-8}$ alkyl groups.

9. A process as claimed in claim 7 wherein the organic groups, $R^1$, $R^2$, $R^3$, $R^4$, $R^5$, $R^6$, $R^7$, $R^8$, $R^9$, $R^{10}$, $R^{11}$ and $R^{12}$ are associated with their respective $R^0$ carbon atom so as to form composite groups which are at least as sterically hindering as t-butyl.

10. A process as claimed in claim 7 wherein the linking groups, $L^1$ and $L^2$, are methylene.

11. A process as claimed in claim 7 wherein the bidentate ligand is selected from α,α'-bis(di-t-butylphosphino)-o-xylene, α,α'-bis(dineopentyl phosphino)-o-xylene and 2,3-bis-(di-t-butylphosphinomethyl)naphthalene.

12. A process for the production of methyl propionate comprising the steps of:

(i) forming a gaseous phase from an ethylene feed stream and a carbon monoxide feed stream;

(ii) contacting the gaseous phase with a catalyst system within a liquid phase comprising methanol, a solvent and a catalyst system comprising palladium, or a compound thereof, a phosphine ligand and a source of anions; and (iii) reacting the ethylene with the carbon monoxide in the presence of the methanol and of the catalyst system;

characterised in that the ethylene feed stream and carbon monoxide feed stream provide a molar ratio of ethylene to carbon monoxide in the gaseous phase which is greater than 1:1.

13. The process of claim 1, wherein said phosphine ligand is a bidentate phosphine ligand.

14. The process of claim 7, wherein said optionally substituted aryl moiety is selected from the group consisting of phenyl, naphthalene, biphenylene and indene.

15. The process of claim 1, wherein said process is a process for the production of propionic acid or propionate esters.

16. A process of claim 1, wherein the molar ratio of the ethylene to the carbon monoxide in the gaseous phase is at least 1.08:1.

17. A process of claim 1, wherein the molar ratio of the ethylene to the carbon monoxide in the gaseous phase is at least 1.8:1.

18. A process of claim 1, wherein the molar ratio of the ethylene to the carbon monoxide in the gaseous phase is at least 3.6:1.

19. A process of claim 1, wherein the molar ratio of the ethylene to the carbon monoxide in the gaseous phase is at least 7:1.

* * * * *

UNITED STATES PATENT AND TRADEMARK OFFICE
CERTIFICATE OF CORRECTION

PATENT NO. : 6,284,919 B1
DATED : September 4, 2001
INVENTOR(S) : Jean Margaret Pearson et al.

It is certified that error appears in the above-identified patent and that said Letters Patent is hereby corrected as shown below:

<u>Column 8,</u>
Line 20, replace "(iii)" with -- (i) --.
Line 22, replace "(iv))" with -- (ii) --.

Signed and Sealed this

First Day of June, 2004

JON W. DUDAS
*Acting Director of the United States Patent and Trademark Office*